US00PP27935P2

(12) United States Plant Patent
Irie

(10) Patent No.: US PP27,935 P2
(45) Date of Patent: Apr. 25, 2017

(54) ***HYDRANGEA* PLANT NAMED 'H21-3'**

(50) Latin Name: *Hydrangea macrophylla*
Varietal Denomination: H21-3

(71) Applicant: Ryoji Irie, Kyoto (JP)

(72) Inventor: Ryoji Irie, Kyoto (JP)

( * ) Notice: Subject to any disclaimer, the term of this patent is extended or adjusted under 35 U.S.C. 154(b) by 57 days.

(21) Appl. No.: 14/545,874

(22) Filed: Jun. 30, 2015

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Keith Robinson
(74) *Attorney, Agent, or Firm* — Penny J. Aguirre

(57) ABSTRACT

A new cultivar of *Hydrangea macrophylla* plant named 'H21-3' that is characterized by its large sterile flowers that are star shaped and dark pink in color, its large inflorescences made up of double sterile flowers with numerous layers of sepals that extend down the pedicel, its very long bloom season, and its strong stems.

2 Drawing Sheets

Botanical classification: *Hydrangea macrophylla.*
Varietal denomination: 'H21-3'.

BACKGROUND OF THE INVENTION

The present invention relates to a new and distinct cultivar of *Hydrangea macrophylla* and will be referred to hereafter by its cultivar name, 'H21-3'. 'H21-3' represents a new bigleaf *hydrangea*, a perennial shrub grown for landscape use.

'H21-3' was derived from an ongoing controlled breeding program directed by the Inventor that focuses on developing new cultivars of bigleaf *hydrangeas* with unique flower colors and double flowers. 'H21-3' arose from a cross made by the Inventor in Kyoto, Japan in May of 2008 between a *Hydrangea macrophylla* plants 'Yamaajisai' (not patented) as the female parent and '97 Pyra' (not patented) as the male parent. 'H21-3' was selected as a single unique plant from amongst the resulting seedlings in May of 2010.

Asexual propagation of the new cultivar was first accomplished by stem cuttings by the Inventor in Kyoto, Japan in July of 2010. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'H21-3' as a unique cultivar of *Hydrangea macrophylla.*

1. 'H21-3' exhibits large sterile flowers that are star shaped and dark pink in color.
2. 'H21-3' exhibits large inflorescences made up of double sterile flowers with numerous layers of sepals that extend down the pedicel.
3. 'H21-3' exhibits a very long bloom season, flowering from late spring through the summer in The Netherlands.
4. 'H21-3' exhibits strong stems.

The female parent of 'H21-3, 'Yamaajisai', differs from 'H21-3' in having smaller flowers that are lighter pink in color and in having weaker stems. The male parent of, 'H21-3', '97 Pyra', differs from 'H21-3' in having stems that are longer and weaker, in having a larger overall plant size, and in having a bloom season that commences later in the season. 'H21-3' can be most closely compared to the *Hydrangea macrophylla* cultivars 'RIE 09' (U.S. Plant Pat. No. 16,613) and 'Inspire' (U.S. Plant Pat. No. 26,824). Both are similar to 'H21-3' in having double flowers. 'RIE 09' differs from 'H21-3' in having sterile flowers that are lighter pink in color with fewer layers of sepals and in having a shorter bloom period. 'Inspire' differs from 'H21-3' in having sterile flowers that are lighter pink in color with fewer layers of sepals and in having broader leaves.

BRIEF DESCRIPTION OF THE DRAWINGS

The accompanying colored photographs illustrate the overall appearance and distinct characteristics of the new *Hydrangea*, 'H21-3'. The photographs were taken of a two year-old plant of 'H21-3' as grown under greenhouse conditions with ambient light in a 15 cm container in De Kwakel, The Netherlands.

The photograph in FIG. 1 provides a side view of a plant of 'H21-3' in bloom.

Figure 1:
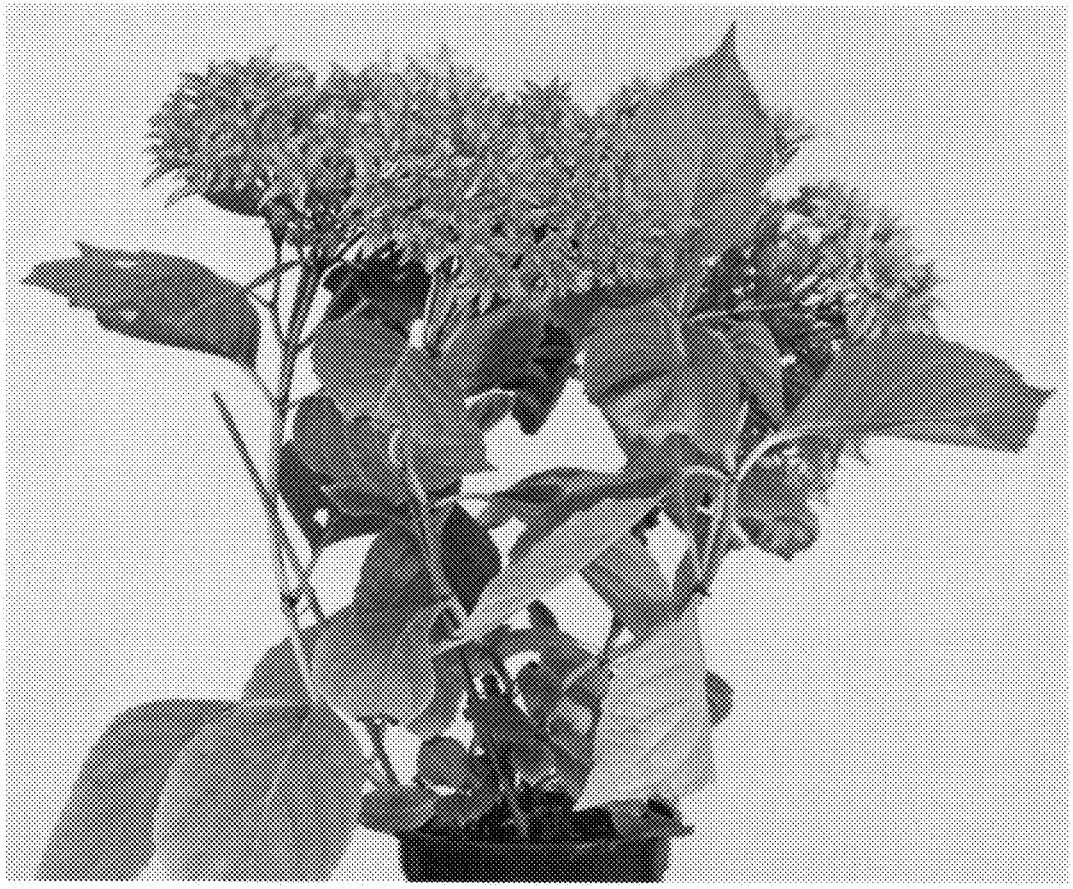
Figure 2:
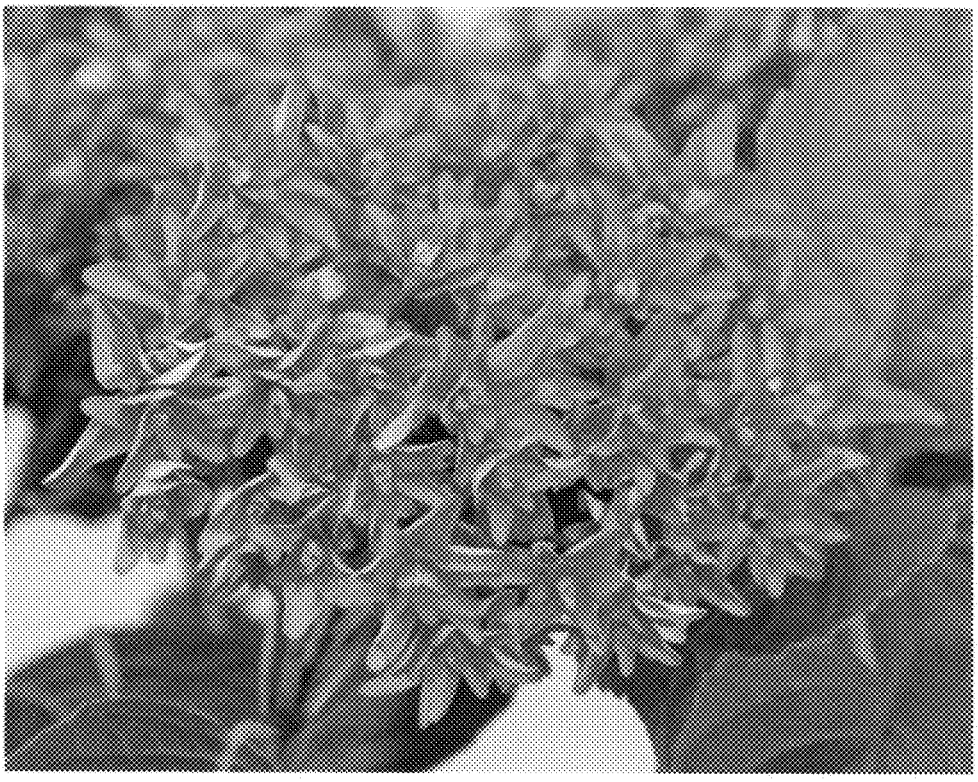

The photograph in FIG. 2 provides a close-up view of an inflorescence of 'H21-3'.

Figure 3:
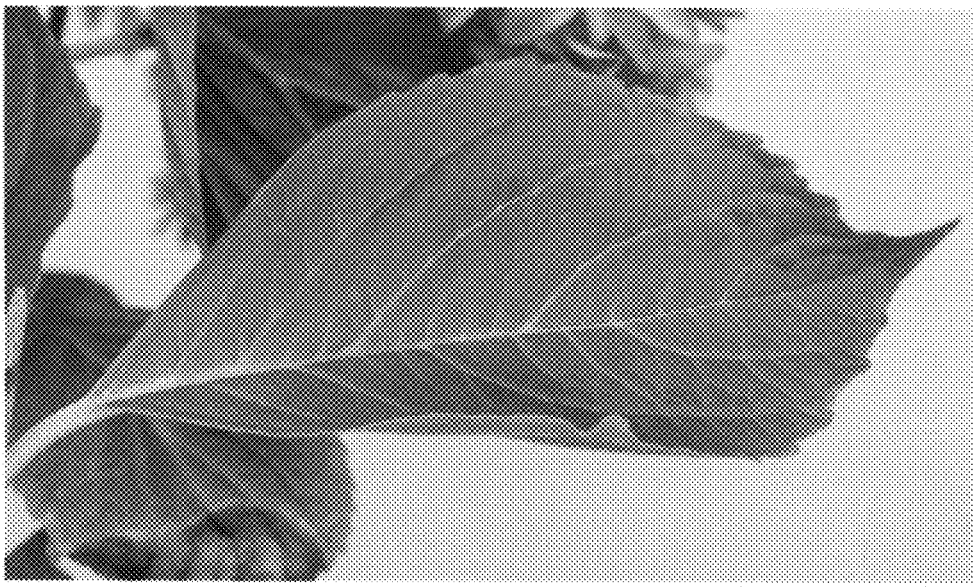

The photograph in FIG. 3 provides a close-up view of a leaf of 'H21-3'.

The colors in the photographs may differ slightly from the color values cited in the detailed botanical description, which accurately describe the colors of the new *Hydrangea.*

BOTANICAL DESCRIPTION OF THE PLANT

The following is a detailed description of two year-old plants as grown under greenhouse conditions with ambient light in 15-cm containers in De Kwakel, The Netherlands.

Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Late spring through summer in The Netherlands.

*Plant type.*—Deciduous shrub, mophead type *Hydrangea.*

*Plant habit.*—Broadly upright, inverted triangular.

*Height and spread.*—An average of 39.5 cm in height and 57.8 cm in diameter.

*Hardiness.*—At least to U.S.D.A. Zones 4 to 9.

*Diseases resistance.*—No susceptibility and resistance to diseases has been observed.

*Root description.*—Fine and fibrous.

*Plant vigor.*—Moderate to high.

Growth and propagation:

*Propagation.*—Stem cuttings.

*Time required for root initiation.*—About 4 weeks at an average temperature of 18° C. (night)/20° C. (day).

*Time required for root development.*—About 3 months to fully develop as a young plant when grown under greenhouse conditions at an average temperature of 18° C. (night)/20° C. (day).

*Time required to a produce a salable crop.*—About 12 months from propagation to a small saleable plant.

*Growth rate and vigor.*—Moderate to high.

Stem description:

*Stem shape.*—Round.

*Stem strength.*—Moderately strong.

*Stem aspect.*—Upright to an average angle of 60°.

*Stem color.*—Immature stems; 144C, mature stems; 199B to 199C, both stems are a blend between N186C and 200A at the nodes.

*Stem size.*—An average of 23.3 cm (excluding the inflorescence) in length and 6 mm in diameter.

*Stem surface.*—Immature surface is moderately to densely covered with oblong lenticels, an average of 1.5 mm in length and 0.75 mm in width, N186C in color, mature stems are smooth and glabrous, fasciation absent.

*Branching.*—Moderately freely branching, including basal branching, with an average of 5 basal branches as grown in a 15-cm container, branching improves with pinching.

*Internode length.*—An average of 6 cm.

Foliage description:

*Leaf shape.*—Elliptic to obovate.

*Leaf arrangement.*—Opposite.

*Leaf division.*—Simple.

*Leaf number.*—An average of 6 (3 pairs) per lateral branch.

*Leaf base.*—Attenuate.

*Leaf apex.*—Apiculate with tip an average of 1.5 cm in length.

*Leaf margins.*—Serrate, lobing absent.

*Leaf venation.*—Pinnate, upper and lower surfaces; 145A to 145B in color.

*Leaf size.*—An average of 14.8 cm in length and 9.1 cm in width.

*Leaf attachment.*—Petiolate.

*Leaf surface.*—Upper surface; very slightly glossy and slightly rugose, lower surface very slightly glossy.

*Leaf color.*—Variegation absent, immature upper surface; a blend between 144A and N144C, immature lower surface; 144B, mature upper surface; 143A, mature lower surface; 144A.

*Petioles.*—An average of 3.2 cm in length and 3.5 mm in diameter, upper and lower surface color; 145A, surface is smooth and slightly glossy.

Inflorescence description:

*Inflorescence type.*—Flattened globular, mophead, compound corymb of rotate-shaped double sterile flowers composed of an average of 19 sepals, very conspicuous.

*Lastingness of inflorescence.*—Sterile and fertile flowers; an average of 3 weeks in peak color, persistent.

*Inflorescence number.*—One per lateral stem.

*Inflorescence size.*—An average of 15.4 cm in height and 18.5 cm in diameter.

*Flower number.*—An average of 120 sterile flowers and an average of 60 fertile flowers.

*Flower fragrance.*—None.

*Flower aspect.*—Sterile flowers; upright and outward, fertile flowers; upright.

*Flower size.*—Sterile flowers; an average of 4.7 cm in diameter and 2.7 cm in depth, fertile flowers; an average of 6 mm in diameter and 8 mm in depth.

*Flower shape.*—Sterile flowers; rotate, star-shaped, fully double with sepals extending down the petiole, fertile flowers; obcordate, formed by a semi-double structure of sepals.

*Flower buds.*—Fertile flowers; an average of 4 mm in length and 3 mm in diameter, obovate in shape, 144B to 144C in color, sterile flowers; an average of 1 cm in length and 8 mm in diameter, obcordate in shape, 149C, tinged towards the top 54B to 54C, all buds have a glabrous surface.

*Peduncles.*—An average of 3 cm in length and 2 mm in diameter, surface smooth and glabrous, 144C in color.

*Pedicels.*—Sterile flowers; up to 4.4 cm in length and 1.75 mm in diameter, held at an average angle of 35° to vertical, 70B in color, moderate strength, dull and moderately covered with very short small hairs average length of 0.2 mm and NN155C in color, fertile flowers; average of 1.5 mm in length and 0.75 mm in diameter, held at an average angle of 30° to peduncle, 144B in color, moderate strength, smooth surface.

*Petals.*—Sterile and fertile flowers; not present.

*Sepals.*—Sterile flowers; an average of 19, calyx is an average of 4.7 cm in diameter, rotate in arrangement and stretching along the petiole, both surfaces smooth and dull, ovate to narrow ovate in shape, margin is entire, tip obtuse, attenuate base, an average of 1.8 cm in length and 9 mm in width, color: upper surface color when opening; 58B to 58C, tip slightly suffused with 53D, center is 149C, lower surface color when opening; 54B to 54C, center is 149C, upper surface color when fully open; 62A, tip is 59D, lower surface when fully open; 63C, upper surface fading to 144B to 145B, irregularly flushed 68D, main vein at the base is 67D, lower surface fading to 146D, main vein at the base is 67D, fertile flowers; average of 12, rotate and semi-double in arrangement, both surfaces smooth and moderately glossy, ovate in shape, margin is entire, acute tip, cuneate base, an average of 5 mm in length and 2 mm in width, color of upper and lower surfaces when opening and fully open is 144A, not fading.

Reproductive organs:

*Androecium.*—Sterile flowers; not present, fertile flowers; androecium rudimentary and dries out when maturing.

*Gynoecium.*—Sterile flowers; an average of 3 pistils, an average of 1 mm in length, stigma is club-shaped and 150D in color, style is about 0.5 mm in length and 145A in color, ovary is 150C in color, fertile flowers; no gynoecium present.

*Fruit and seed.*—No seeds or fruit observed.

It is claimed:

1. A new and distinct cultivar of *Hydrangea* plant named 'H21-3' substantially as herein illustrated and described.

* * * * *